US00PP11687P

United States Patent [19]

Trees

[11] Patent Number: Plant 11,687

[45] Date of Patent: Dec. 12, 2000

[54] GERANIUM PLANT NAMED 'BALCOLINK'

[75] Inventor: Scott C. Trees, Nipomo, Calif.

[73] Assignee: Ball FloraPlant, a division of Ball Horticultural Co., West Chicago, Ill.

[21] Appl. No.: 09/257,099

[22] Filed: Feb. 22, 1999

[51] Int. Cl.[7] ..... A01H 5/00

[52] U.S. Cl. ..... Plt./332

[58] Field of Search ..... Plt./332

*Primary Examiner*—Howard J. Locker
*Assistant Examiner*—Wendy A Baker
*Attorney, Agent, or Firm*—C. A. Whealy

[57] ABSTRACT

A new and distinct cultivar of Geranium plant named 'Balcolink', characterized by its numerous pink-colored semi-double flowers; upright and trailing growth habit; basal branching; vigor; and medium green leaves with a dark maroon-colored zonation pattern.

1 Drawing Sheet

BACKGROUND OF THE INVENTION

The present invention relates to a new and distinct cultivar of Geranium plant, botanically known as *Pelargonium peltatum*, and hereinafter referred to by the cultivar name Balcolink.

The new Geranium is a product of a planned breeding program conducted by the Inventor in Arroyo Grande, Calif. The objective of the breeding program was to develop new cultivars with freely-branching and vigorous growth habit, medium or dark green-colored foliage, uniform flowering, and interesting flower and foliage colors.

The new Geranium originated from a cross made by the Inventor of the proprietary *Pelargonium peltatum* selection BFP-1137 as the male, or pollen parent, with the proprietary *Pelargonium peltatum* selection BFP-1370 as the female, or seed parent. The cultivar Balcolink was discovered and selected by the Inventor as a flowering plant within the progeny of the stated cross in a controlled environment in Arroyo Grande, Calif., in December, 1996.

Asexual reproduction of the new cultivar by terminal cuttings taken at Arroyo Grande, Calif., has shown that the unique features of this new Geranium are stable and reproduced true to type in successive generations of asexual reproduction.

SUMMARY OF THE INVENTION

The following traits have been repeatedly observed and are determined to be the unique characteristics of 'Balcolink'. These characteristiics in combination distinguish 'Balcolink' as a new and distinct cultivar:

1. Numerous pink-colored semi-double flowers.
2. Upright and trailing growth habit.
3. Basal branching and vigorous.
4. Medium green leaves with dark maroon zonation pattern.

The new Geranium differs from plants of its sibling cultivar, 'Balcolav', U.S. Plant patent application Ser. No. 09/257,091, in plant habit, number of flowers per umbel, flower form and flower color.

The new Geranium differs from plants of its sibling cultivar, 'Balcolburg', U.S. Plant patent application Ser. No. 09/257,098, in plant height, umbel size, flower form and flower color.

The new Geranium differs from plants of its sibling cultivar, 'Balcolilac', U.S. Plant patent application Ser. No. 09/257,088, in plant height, leaf size, leaf sonation pattern, number of flowers per umbel, flower form, flower size, number of petals per flower and flower color.

The new Geranium can be compared to the cultivar, Nicole, disclosed in U.S. Plant Pat. No. 7,358. However, in side-by-side comparisons conducted in Arroyo Grande, Calif., plants of the new Geranium differ from plants of the cultivar Nicole in the following characteristics:

1. Plants of the new Geranium are more vigorous and larger than plants of the cultivar Nicole.
2. Plants of the new Geranium have larger but fewer flowers per umbel than plants of the cultivar Nicole.
3. Plants of the new Geranium have fewer petals per flower than plants of the cultivar Nicole.
4. Flower color of the new Geranium is slightly pink than flower color of the cultivar Nicole.

A detailed comparison of plants of the cultivar Balcolink and the cultivar Nicole, as grown side by side, appears in Chart A at the end of the specification.

BRIEF DESCRIPTION OF THE PHOTOGRAPH

The accompanying colored photograph illustrates the overall appearance of the new cultivar, showing the colors as true as it is reasonably possible to obtain in colored reproductions of this type. The photograph comprises a side perspective view of a typical plant of 'Balcolink'. Flower and foliage colors in the photograph may appear different from the actual colors due to light reflectance.

DETAILED BOTANICAL DESCRIPTION

The cultivar Balcolink has not been observed under all possible environmental conditions. The phenotype may vary somewhat with variations in environment such as temperature and light intensity, without, however, any variance in genotype. The following observations, measurements and comparisons describe plants grown in 10-cm pots in Arroyo Grande, Calif., under commercial practice in a glass-covered greenhouse with day temperatures about 20 to 22° C., night temperatures about 18 to 20° C. and light levels generally about 2,500 to 3,000 footcandles.

In the following description, color references are made to The Royal Horticultural Society Colour Chart except where general terms of ordinary dictionary significance are used.

Botanical classification: *Pelargonium peltatum* cultivar Balcolink.

Parentage:

*Male parent*.—Proprietary *Pelaronium peltatum* selection BFP-1137.

*Female parent*.—Proprietary *Pelargonium peltatum* selection BFP-1370.

Propagation:

*Type cutting*.—Terminal cuttings.

*Time to initiate roots*.—About 7 days at 18° C.

*Time to develop roots*.—About 21 days at 18° C.

*Rooting habit*.—Fibrous and freely branching.

Plant description:

*General appearance*.—Upright and trailing growth habit. Appropriate for 10-cm and larger containers.

*Crop time*.—Starting with a rooted cutting, about twelve weeks are required to produced a finished flowering plant in 10-cm container.

*Growth and branching habit*.—Vigorous and basally branching with about three to five lateral branches at the base. Pinching, that is, removal of terminal apices, enhances branching.

*Plant height* (*to top of foliage*).—About 25 to 27 cm.

*Plant width*.—About 20 to 26 cm.

*Lateral branches*.—Length: About 17 to 21 cm. Internode length: About 2.6 to 3.8 cm. Color: 144C.

*Foliage description*.—Leaves simple, generally symmetrical, abundant, opposite. Quantity of leaves per lateral branch: About 12 to 15. Length: About 3.5 to 4.5 cm. Width: About 5.8 to 6.5 cm. Shape: Peltate, palmately lobed. Apex: Pointed. Base: Cordate. Venation: Palmate. Texture: Leathery; shiny; slightly pubescent. Color: Fully expanded foliage, upper surface: Close to 137A; zonation pattern, 187A in color, about 7 mm in width. Fully expanded foliage, lower surface: 137C. Venation, upper surface: 137C. Venation, lower surface: 137C. Petiole: Length: About 3.2 to 3.7 cm. Diameter: About 1.8 to 2.2 mm. Color: 137C.

Flower description:

*Flower type and habit*.—Pink-colored flowers. Freely and continuously flowering. Flowers arranged in substantially hemispherical umbels arising from apical leaf axils. Umbels displayed above or beyond the foliage. At full flowering, usually about six or seven open umbels and three or four developing umbels per plant. Flowers semi-double and round. Umbels persistent. Not fragrant.

*Flowering season*.—Year-round under greenhouse conditions. In the garden, flowering is continuous from spring until fall.

*Umbels*.—Number of flowers per umbel: About 8 to 10. Diameter: About 8.3 to 10 cm. Height: About 6 to 6.5 cm.

*Flowers*.—Diameter: About 5.5 to 6 cm. Depth (height): About 8 to 10 mm.

*Flower buds*.—Length: About 1.4 to 1.7 cm. Diameter: About 6 to 10 mm. Shape: Oval, pointed.

*Petals*.—Quantity: About 7 to 9 petals and about 2 to 4 elongated petaloids per flower. Arrangement: Imbricate. Length: About 2.7 to 3.4 cm. Width: About 2.1 to 2.4 cm. Shape: Obovate. Apex: Rounded. Base: Attenuate. Margin: Entire. Texture: Smooth. Color, fully opened flowers: Upper petals, upper surface: Background, 73A; venation, 59C, forming a prominent splotch distally; interveinal, 73D. Upper petals, lower surface: 62C; venation, 63B. Lower petals, upper surface: 73A. Lower petals, lower surface: 63B.

*Sepals*.—Quantity: About 5, not imbricate. Length: About 1.4 to 1.5 cm. Width: About 3 to 5 mm. Shape: Lanceolate. Apex: Pointed. Margin: Entire. Texture: Pilose. Color: Upper surface: 146A. Lower surface: 146B.

*Peduncle* (*umbel stem*).—Length: About 13 to 17 cm. Angle: Erect. Strength: Strong. Texture: Slightly pubescent. Color: 146A.

*Pedicel* (*individual flower stem*).—Length: About 2.5 to 3.6 cm. Texture: Pubescent. Color: 146B.

*Reproductive organs*.—Androecium: Anther size: About 2 to 3 mm. Anther color: 79B. Pollen color: 169A. Gynoecium: Ovary color: Green.

Disease resistance: Resistance to pathogens common to Pelargonium has not been observed.

Seed development: Seed production has not been observed.

CHART A

| CHARACTERISTIC | 'BALCOLINK' | 'NICOLE' |
|---|---|---|
| PLANT HABIT | Upright, trailing | Upright, trailing |
| VIGOR | Vigorous | Moderately vigorous |
| PLANT HEIGHT (to top of foliage) | About 25 to 27 cm | About 21 to 24 cm |
| PLANT WIDTH | About 20 to 26 cm | About 14 to 18 cm |
| NUMBER OF FLOWERS PER UMBEL | About 8 to 10 | About 11 to 13 |
| FLOWER DIAMETER | About 5.5 to 6 cm | About 4.5 to 5.5 cm |
| PETAL QUANTITY PER FLOWER | About 7 to 9 | About 11 to 13 |
| PETAL COLOR, UPPER PETALS, UPPER SURFACE | Background, 73A; venation, 59C; interveinal, 73D | Background, 62A; venation, 61B; interveinal, 62C; spot, 38D |
| PETAL COLOR, UPPER PETALS, LOWER SURFACE | 62C; venation, 63B | 62C; venation, 61C |
| PETAL COLOR, LOWER PETALS, UPPER SURFACE | 73A | Background, 62A; spot, 38D |
| PETAL COLOR, LOWER PETALS, LOWER SURFACE | 63B | 62C |

It is claimed:

1. A new and distinct cultivar of Geranium plant named 'Balcolink', as illustrated and described.

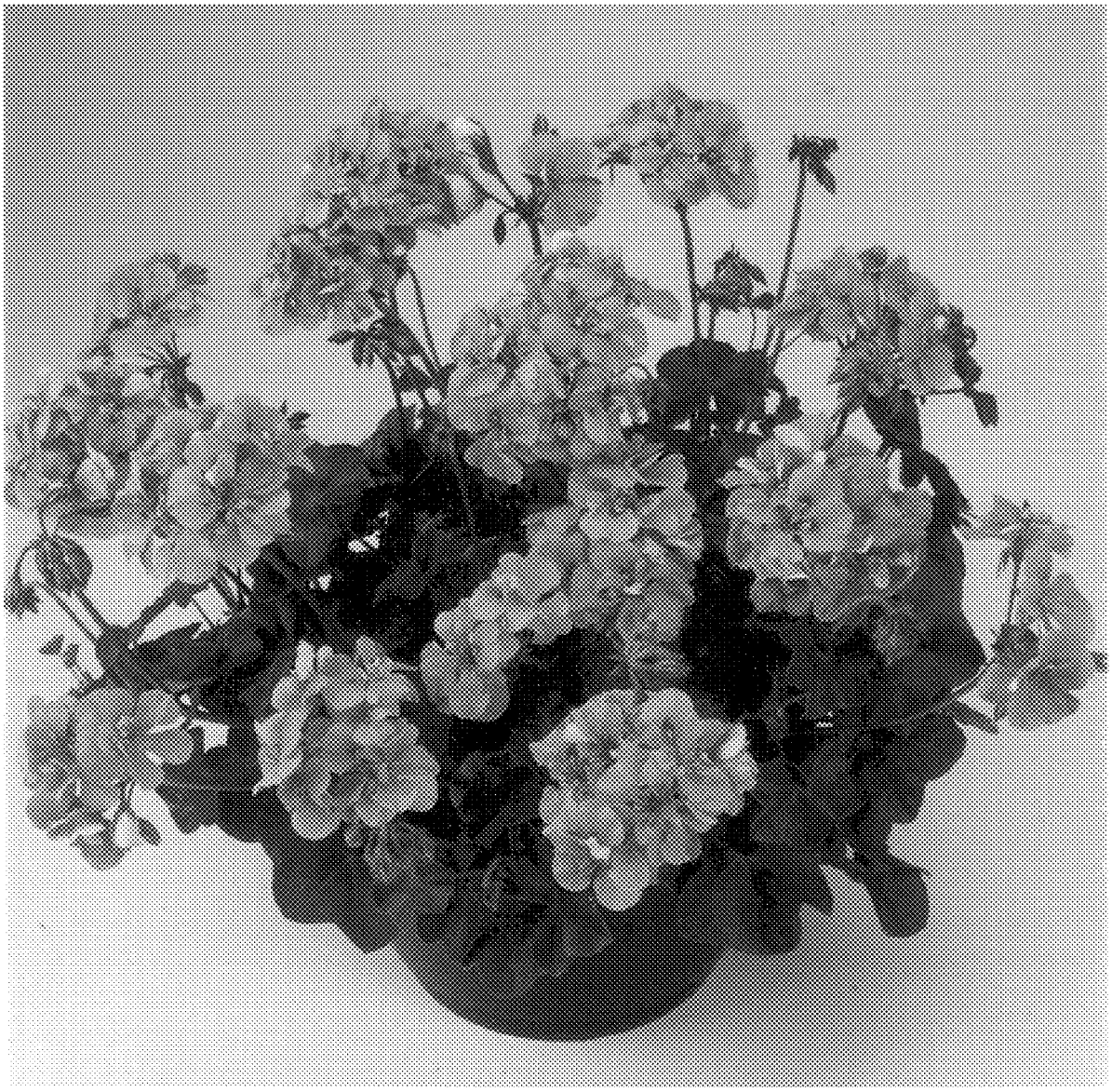

* * * * *